(12) United States Patent
Von Oepen et al.

(10) Patent No.: US 8,261,420 B2
(45) Date of Patent: Sep. 11, 2012

(54) METHOD AND APPARATUS FOR REDUCING STRESS DURING STENT MANUFACTURE

(75) Inventors: Randolf Von Oepen, Los Altos Hills, CA (US); Travis Richard Yribarren, San Mateo, CA (US); Richard Roy Newhauser, Redwood City, CA (US); Rainer Bregulla, Balingen (DE)

(73) Assignee: Abbott Laboratories, Abbott Park, IL (US)

( * ) Notice: Subject to any disclaimer, the term of this patent is extended or adjusted under 35 U.S.C. 154(b) by 1156 days.

(21) Appl. No.: 12/119,945

(22) Filed: May 13, 2008

(65) Prior Publication Data
US 2009/0282669 A1    Nov. 19, 2009

(51) Int. Cl.
*B23P 17/00* (2006.01)
*A61F 2/06* (2006.01)

(52) U.S. Cl. ............... 29/446; 29/447; 29/235; 29/270; 29/282; 29/283.5; 29/284

(58) Field of Classification Search ............. 29/446, 29/447, 270, 272, 282, 283.5, 284, 235, 242
See application file for complete search history.

(56) References Cited

U.S. PATENT DOCUMENTS

| | | | | |
|---|---|---|---|---|
| 1,319,297 | A * | 10/1919 | Limacher | 215/11.1 |
| 1,363,522 | A * | 12/1920 | Leitch | 29/235 |
| 1,408,039 | A * | 2/1922 | Snyder | 29/235 |
| 2,038,840 | A * | 4/1936 | Hall | 29/235 |
| 2,830,361 | A * | 4/1958 | Bruner | 29/235 |
| 4,466,166 | A * | 8/1984 | Hogarth | 29/235 |
| 5,074,023 | A * | 12/1991 | Decker et al. | 29/450 |
| 6,049,960 | A * | 4/2000 | Pilling et al. | 29/450 |
| 6,444,913 | B1 * | 9/2002 | Kao | 174/73.1 |

* cited by examiner

*Primary Examiner* — Jermie Cozart
(74) *Attorney, Agent, or Firm* — Baker Botts LLP

(57) ABSTRACT

The invention relates to a method and apparatus of reducing stress during stent manufacture. Particularly, the invention is directed to a method and apparatus for expanding a stent using primarily radial loads thereby reducing the stresses that are generated due to the axial loads applied during loading of the stent onto a mandrel or other expansion device. The method of the invention provides for the stepwise expansion of shape memory stents, while reducing the overall stresses that the stent encounters, and thereby improving manufacturing yields due to fractured struts during expansion.

10 Claims, 4 Drawing Sheets

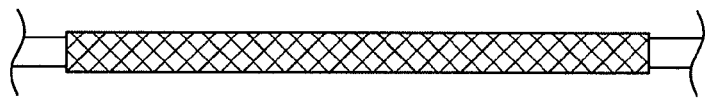
FIG. 4F
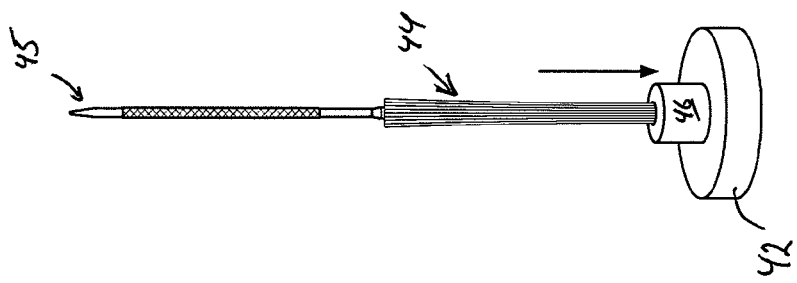
FIG. 4E  FIG. 4D
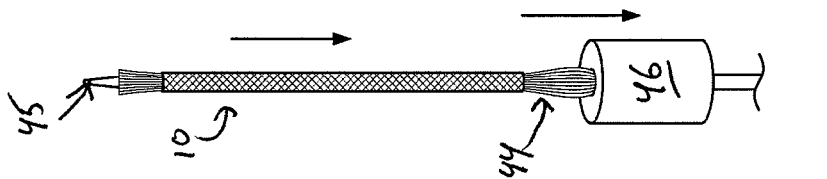
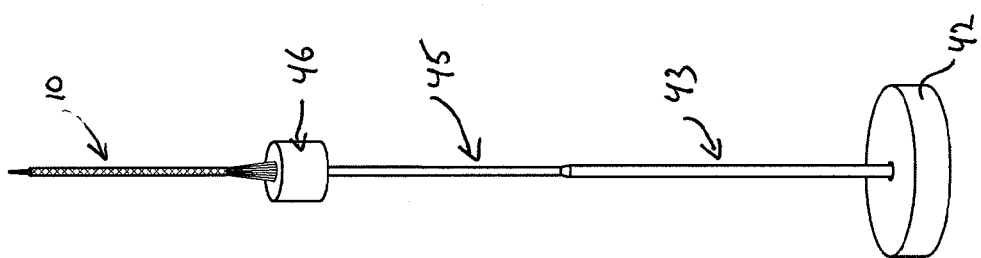
FIG. 4C
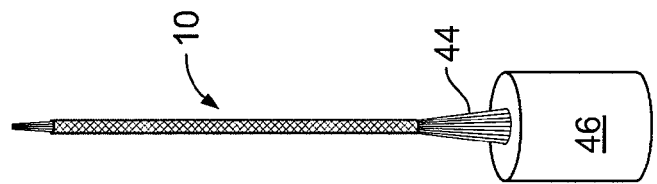
FIG. 4B
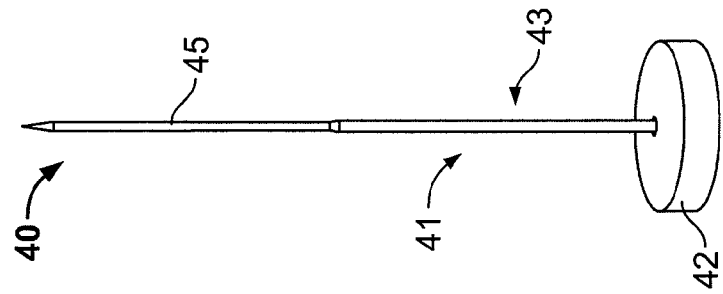
FIG. 4A

METHOD AND APPARATUS FOR REDUCING STRESS DURING STENT MANUFACTURE

BACKGROUND OF THE INVENTION

1. Field of the Invention

The invention relates to a method and apparatus for reducing stress during stent manufacture. Particularly, the invention is directed to a method and apparatus for expanding a stent using primarily radial loads thereby reducing the stresses that are generated due to the axial loads applied during loading of the stent onto a mandrel or other expansion device. The method of the invention provides for the stepwise expansion of shape memory stents, while reducing the overall stresses that the stent encounters, and thereby improving manufacturing yields due to fractured struts during expansion.

2. Description of Related Art

Cardiovascular disease is prevalent in the United States and in other parts of the world. One manifestation of cardiovascular disease is atherosclerosis, which is the buildup of plaque (or fatty deposits) on the walls of blood vessels, such as coronary arteries. This buildup of plaque can grow large enough to reduce blood flow through the blood vessel. Serious damage results when an area of plaque ruptures and forms a clot, which travels to another part of the body. If the blood vessels that feed the heart are blocked, a heart attack results. If the blood vessels to the brain are blocked, a stroke results. Thus, atherosclerosis can be fatal for some people.

Typically, physicians treat atherosclerosis by implanting a tubular endoprothesis such as a stent at the narrowed or blocked segment of the blood vessel, which widens and holds open the blood vessel. To perform this procedure the stent is delivered to the site of the lesion in the blood vessel by a catheter assembly, otherwise known as a stent delivery device. The stent delivery device enters the vasculature of the patient through the femoral artery and travels through a tortuous path to the site of the lesion. The physician positions the stent across the lesion and deploys the stent so that the stent forces the plaque against the inside wall of the blood vessel (or lumen) and maintains its expanded configuration so that the patency of the blood vessel is maintained.

The term "stent" has come into widespread use to denote any of a large variety of spring-like support structures, in the form of a tube which is open at both ends, which can be implanted inside a blood vessel or other tubular body conduit, to help keep the vessel or conduit open. Stents may be used following balloon angioplasty to prevent restenosis and may, more generally, be used in repairing any of a number of tubular body conduits, such as those in the vascular, biliary, genitourinary, gastrointestinal and respiratory systems, among others, which have narrowed, weakened, distorted, distended or otherwise deformed, typically as a result of any of a number of pathological conditions.

Typically, the stent is delivered inside the body by a catheter that supports the stent in a compacted form as it is transported to the desired site. Upon reaching the site, the stent is expanded so that it engages the walls of the lumen. The expansion mechanism may involve forcing the stent to expand radially outward, for example, by inflation of a balloon carried by the catheter, to inelastically deform the stent and fix it at a predetermined expanded position in contact with the lumen wall. The expansion balloon can then be deflated and the catheter removed.

In another technique, the stent is formed of a highly elastic material that will self-expand after being compacted. During introduction into the body, the stent is restrained in the compacted condition. When the stent has been delivered to the desired site for implantation, the restraint is removed, allowing the stent to self-expand by its own internal elastic restoring force.

An effective stent must possess a number of important and very specific characteristics. Specifically, the stent should be chemically and biologically inert to its surroundings and should not react with, or otherwise stimulate, the living tissues around it. The stent must further be such that it will stay in the correct position and continue to support the tubular body conduit into which it is implanted over extended periods of time. Further, the stent must have the ability to return to its prescribed in-place diameter after the stent diameter has been significantly reduced prior to its insertion, usually tightly wrapped on a catheter, into the tubular body conduit. An example of such a stent in the prior art is disclosed in U.S. Pat. No. 5,827,321, the entirety of which is hereby incorporated by reference.

A variety of methods and systems are known for manufacturing stents, and for imparting a desired geometry onto the stent structure. Conventional methods of manufacturing stents required the expansion of the stents from a smaller diameter, or "as cut" position, to a larger diameter corresponding to the stent configuration as deployed in the patient. This expansion is typically performed by the intricate process of providing an initial heat treatment stage followed by the forcible sliding of the stents over a mandrel, and providing a subsequent heat treatment stage.

Such conventional methods and systems generally have been considered satisfactory for their intended purpose. Recently, however, there is a need to reduce or eliminate the stress induced on the stent during application of the axial force required to forcibly slide the stent over the mandrel. The stresses generated within the stent material as the stent encounters radial loads and axial loads while being placed onto the mandrels can result in localized deformities such as strut fracture, kink, and flare. The presence of such deformities can jeopardize the structural integrity and performance characteristics of the stent. Further, such deformities can damage tissue in the lumen wall of the patient. Consequently, the conventional methods for expanding stents requires extensive quality control and results in low product yield.

Additionally, the prior art method of expanding stents is disadvantageous in that the process must be performed in various discrete stages requiring numerous mandrels of differing sizes to provide incremental expansion in order to avoid damaging the stent. In many instances the requisite tooling and discrete process steps will reach a level that is too burdensome and complex to be performed in a cost effective manner. Examples of such prior art expansion techniques are disclosed in U.S. Pat. No. 6,305,436 and U.S. Pat. No. 6,402,779, each of which is hereby incorporated by reference in their entirety.

As evident from the related art, conventional methods often provide inadequate stent expansion techniques and cost prohibitive systems.

There thus remains a need for an efficient and economic method and system to provide for the stepwise expansion of shape memory stents, while reducing the overall stresses that the stent encounters, and thereby improving manufacturing yields due to fractured struts during expansion.

SUMMARY OF THE INVENTION

The purpose and advantages of the invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a method of manufacturing a medical device comprising forming a stent having a proximal end, a distal end, and a longitudinal axis extending therebetween, the stent having a generally cylindrical shape defining a first stent diameter. An expansion member is inserted into either the proximal or distal end of the stent, with the expansion member extending along the longitudinal axis of the stent and having a first expansion diameter. The expansion member can be radially expanded to a second expansion diameter wherein the radial force exerted by the expansion member on the stent expands the stent to a second stent diameter, the second stent diameter being greater than the first stent diameter.

In one embodiment, the expansion member is a generally tubular member having a proximal end and a distal end defining a length therebetween, wherein the expansion member includes at least one slot extending along the length of the expansion member defining a plurality of expansion blades. Preferably, a first portion of the expansion blades are connected at the proximal end of the expansion member and a second portion of the expansion blades are disconnected at the distal end of the expansion member.

In accordance with an aspect of the invention a tapered mandrel can be axially inserted into a distal end of the expansion member to displace the blades of the expansion member and radially expand the stent to the second stent diameter.

In accordance with another embodiment of the invention, the expansion member can include a plurality of arms arranged in a generally cylindrical configuration, wherein the plurality of arms extend along the longitudinal axis through the proximal and distal ends of the stent. Further, an actuator can operatively engage the plurality of arms at a location proximate to the distal end of the stent to move the arms radially outward and expand the stent to the second stent diameter. Preferably, the actuator can engage each of the plurality of arms simultaneously to provide uniform radial expansion of the arms.

In accordance with an aspect of the invention, an apparatus for expanding the stent includes an expansion member having a plurality of arms arranged in a generally cylindrical configuration with a first expansion diameter for insertion along the longitudinal axis of a stent, wherein the actuator includes an end plate having a cam portion and cam followers. The actuator is configured to operatively engage the plurality of arms to radially expand to a second expansion diameter, the radial force exerted by the radial expansion of the plurality of arms on the stent expands the stent. Preferably, the actuator operatively engages the plurality of arms at a location proximate to a distal end of the stent to move the arms radially outward and expand the stent to the second stent diameter. The actuator radially expands, or displaces radially outward, each of the plurality of arms simultaneously upon rotation of the end plate.

In accordance with another embodiment of the invention, the expansion member can include a plurality of wires extending along the longitudinal axis of the stent, wherein a mandrel is inserted into plurality of wires to radially expand the plurality of wires to a second expansion diameter, the radial force exerted by the radial expansion of the plurality of wires on the stent expands the stent to the second stent diameter. Thereafter, the plurality of wires can be removed while the mandrel remains inserted within the stent. Further, a plurality of stent diameters can be achieved by employing a plurality of differently sized mandrels with a fixed number of wires. Alternatively, a plurality of stent diameters can be achieved by employing a single mandrel with a varying number of wires.

In accordance with an aspect of the invention, an apparatus for expanding a stent comprises a fixture with a mandrel disposed thereon, and an expansion member including a plurality of wires arranged in a generally cylindrical configuration having a first expansion diameter for insertion along the longitudinal axis of a stent having a first stent diameter. At least a portion of the expansion member is drawn over the mandrel to expand the plurality of wires to a second expansion diameter, the second expansion diameter expanding the stent to a second stent diameter. Additionally, the plurality of wires are securely positioned within an anchor portion which includes a hole for receiving at least a portion of the mandrel. The mandrel further includes a wire guide affixed to the mandrel, the plurality of wires extending through the wire guide.

In accordance with still another aspect of the invention, the expansion member can be configured as a tapered mandrel having channels formed in the outer surface thereof, the channels including expansion rods or wires disposed therein which can be displaced radially to expand the stent to the second stent diameter.

Additionally, the stent can be exposed to a temperature below approximately −40 degrees Fahrenheit to place the stent in the martensitic phase. Similarly, the stent can be exposed to a temperature within the range of approximately 175 and 600 degrees Fahrenheit. Preferably, the stent is made from a shape memory material.

It is to be understood that both the foregoing general description and the following detailed description are exemplary and are intended to provide further explanation of the invention claimed.

The accompanying drawing, which is incorporated in and constitutes part of this specification, is included to illustrate and provide a further understanding of the method and system of the invention. Together with the description, the drawing serves to explain the principles of the invention.

BRIEF DESCRIPTION OF THE DRAWINGS

FIGS. 4A-G is a schematic representation of a third embodiment for reducing the stress during expansion of a stent as shown in FIG. 1.

DETAILED DESCRIPTION OF THE INVENTION

Reference will now be made in detail to the various embodiments of the invention, an example of which is illustrated in the accompanying drawing. The method and corresponding steps of the invention will be described in conjunction with the detailed description of the system.

The methods and systems presented herein may be used for imparting a desired shape or contour to a medical endoprosthesis such as a stent. The invention is particularly suited for expanding a stent using primarily radial loads thereby reducing the stresses that are generated due to the axial loads applied during loading of the stent onto a mandrel. For purpose of explanation and illustration, and not limitation, an exemplary embodiment of the system in accordance with the invention is illustrated in the accompanying Figures.

Figure 1:
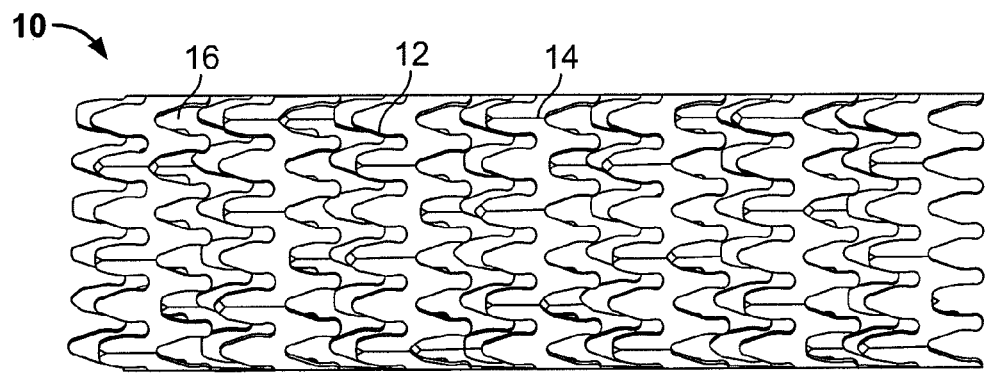
FIG. 1 is a schematic representation of a stent formed in accordance with the invention.

FIG. 1 illustrates an example of a stent 10 formed from a plurality of struts 12, which can be formed in accordance with the invention. The plurality of struts 12 are radially expandable and interconnected by connecting elements 14 that are disposed between the adjacent struts 12, leaving lateral openings or gaps 16 between the adjacent struts 12. The struts 12 and the connecting elements 14 define a tubular stent body having an outer, tissue-contacting surface and an inner surface. The particular geometry of the struts and connecting elements depicted is merely for purpose of explanation. Various stent geometries and configurations such as stents having differing structural properties, variable flexibility, variable radiopacity, as well as various categories of stents (i.e., balloon expandable, self-expanding and drug eluting stents) are contemplated to be within the scope of the invention.

The stents formed in accordance with the invention are preferably made from a shape memory material such as Nitinol (Ni—Ti alloy). In manufacturing the Nitinol stent, the material is first in the form of a tube. Nitinol tubing is commercially available from a number of suppliers. The tubular member is then loaded into a machine that will cut the predetermined pattern of the stent into the tube, as discussed above and as shown in FIG. 1. Machines for cutting patterns in tubular devices to make stents or the like are well known to those of ordinary skill in the art and are commercially available. Such machines typically hold the metal tube between the open ends while a cutting laser, preferably under microprocessor control, cuts the pattern. The pattern dimensions and styles, laser positioning requirements, and other information are programmed into a microprocessor, which controls all aspects of the process. After the stent pattern is cut, the stent is treated and polished using any number of methods or combination of methods well known to those skilled in the art.

Specifically, and in accordance with the invention, an apparatus and method of expanding a stent is provided which uses primarily radial loads, thereby reducing the stresses that are imparted onto the stent due to the axial loads applied during loading of the stent onto a mandrel or other expansion device. The invention includes an apparatus and corresponding method of expanding a stent comprising forming a stent having a proximal end, a distal end, and a longitudinal axis extending therebetween, with the stent having a generally cylindrical shape defining an initial unexpanded stent diameter.

An expansion member is inserted into either the proximal or distal end of the stent, with the expansion member extending along the longitudinal axis of the stent and having an initial unexpanded diameter. The initial unexpanded diameter of the expansion member being less than the initial unexpanded diameter of the stent to allow for insertion of the expansion member into the stent. The expansion member can then be radially expanded to a second expansion diameter wherein the radial force exerted by the expansion member on the stent consequently expands the stent to a second stent diameter, wherein the second stent diameter is greater than the first stent diameter. Typically, the initial diameter of the stent is approximately 3 millimeters and the expanded diameter is approximately 6 millimeters, though it is understood that the invention could be applied to stents of any desired size.

Figure 2A:
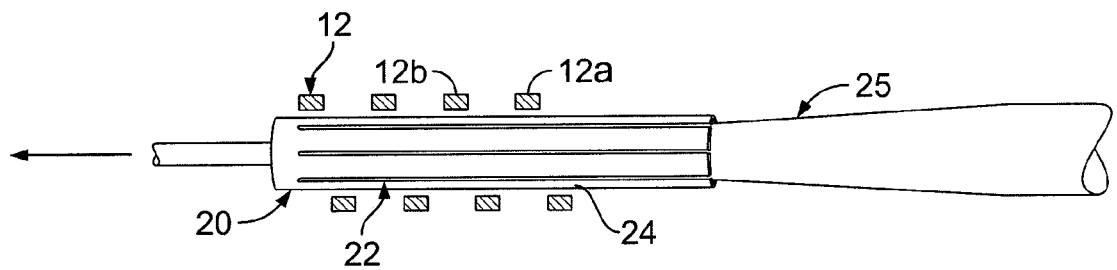
FIG. 2A is a schematic representation of a first embodiment for reducing the stress during expansion of a stent as shown in FIG. 1, the stent shown in the unexpanded stage.
Figure 2B:
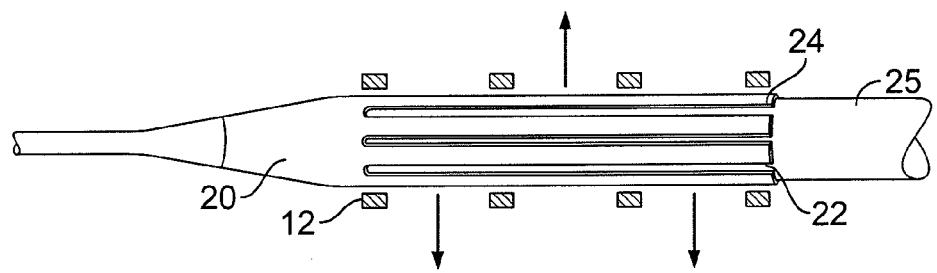
FIG. 2B is a schematic representation of the embodiment shown in FIG. 2A, the stent shown in the expanded stage.

In one embodiment of the invention, the expansion member is configured as a generally tubular member which is inserted within the stent, as shown in FIGS. 2A-2B. FIG. 2A illustrates a cross-sectional view of the initial stage of the expansion process wherein the stent (10) and expansion member (20) are in the unexpanded configuration and the stent struts (12) are disposed on the exterior the expansion member (20). In some applications, the initial diameter of the expansion member (20) is approximately equal to the initial diameter of the stent (10) so as to provide an interference fit between the stent and the expansion member. Further, the exterior surface of the expansion member can be coated with a lubricious layer or film to facilitate the insertion of the expansion member, and further reduce any stress induced onto the stent from axial loads. Alternatively, the initial diameter of the expansion member (20) may be significantly less than the initial diameter of the stent (10) to allow for rapid insertion of the expansion member into the stent.

Preferably, the expansion member (20) includes a plurality of channels or slots (22) which define a plurality of expansion blades (24). The expansion member is made of a flexible material which allows for each individual blade (24) to be displaced in a radial direction. The embodiment herein includes slots (22) which do not extend along the entire length of the expansion member (20). Instead, the slots (22) extend along the longitudinal axis of the expansion member from a position proximate to a first or proximal end of the expansion member (20) to the second or distal end of the expansion member. Accordingly, the portion of the blades (24) at distal end of the expansion member (20) are completely disconnected from each other, while the portion of the blades (24) at the proximal end of the expansion member remain integrally connected. Providing a slotted expansion member which is integral and continuous in the radial direction at the proximal end is advantageous in that such a configuration facilitates loading the stent onto the expansion member. For example, the continuous proximal end of the expansion member (20) prevents any errant deflection or displacement of an individual blade (24), thereby preventing the occurrence of accidental snagging or rupture of either the blade or the stent upon insertion of the expansion member into the stent.

In accordance with another aspect of this embodiment, a mandrel (25) can be axially inserted into the distal end of the expansion member (20). Preferably, the mandrel (25) is configured with a gradual taper along the longitudinal axis which imparts an increasing radial expansion force which corresponds to the amount of axial insertion within the expansion member (20). In one example, the tapered mandrel is axially inserted into the distal end of the slotted tube (20) from the smallest diameter to largest diameter such that the taper induces a radial expansion force on the blades (24) to force the blades to open or expand to a larger diameter. This expansion force is in turn transmitted to the stent surface, however the axial insertion force is not significantly transmitted to the stent surface. This reduction in axial force is advantageous in that it reduces the stress realized by the stent and therefore decreases the risk of strut fracture.

In the embodiment illustrated in FIGS. 2A-B, the stent (10) is gradually expanded such that each strut (12) is expanded in sequential order along the longitudinal axis. The struts (12a) located at the most distal end of the stent (10) are expanded first, followed by the proximally adjacent struts (12b). Thus, the expansion of the stent can be tailored to provide a stent having varying expansion diameters along the longitudinal axis. Accordingly, a plurality of mandrels having varying tapers can be employed to provide the varied expansion configurations or particular structural characteristics if so desired.

Further, the operation of inserting the mandrel into the stent can be accomplished by a myriad of manual or automatic apparatus designs. For example, a screw type mechanism could be employed which converts rotational motion of the screw into axial motion to advance the mandrel into the stent. Additionally, various other types of mechanisms including pneumatics, hydraulics, or linear motors can be utilized to ensure that the motion of the mandrel occurs gradually and/or consistently to limit the production of stress spikes within the stent.

In another embodiment of the invention, the expansion member can be configured as a reverse-iris style mechanism. During operation, the end plate is rotated via manual or automatic means to cause movement of the arms about a pivot point or hinge which results in a general opening of the overall expansion member. Particularly, each arm is displaced radially outward, thereby transmitting a predominantly radial expansion force on the surface of the stent to increase the stent diameter.

Figure 3A:
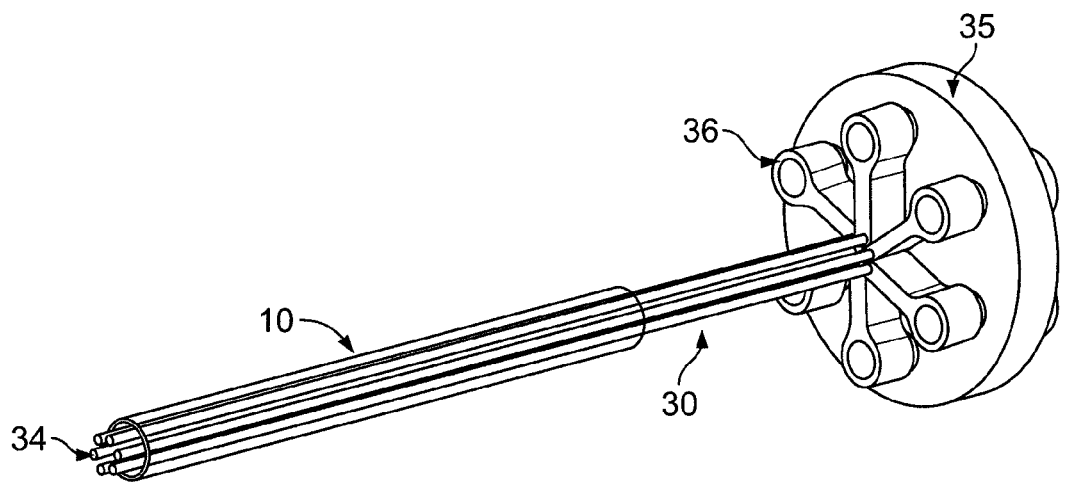
FIG. 3A is a schematic representation of a second embodiment for reducing the stress during expansion of a stent as shown in FIG. 1, the stent shown in the unexpanded stage.
Figure 3B:
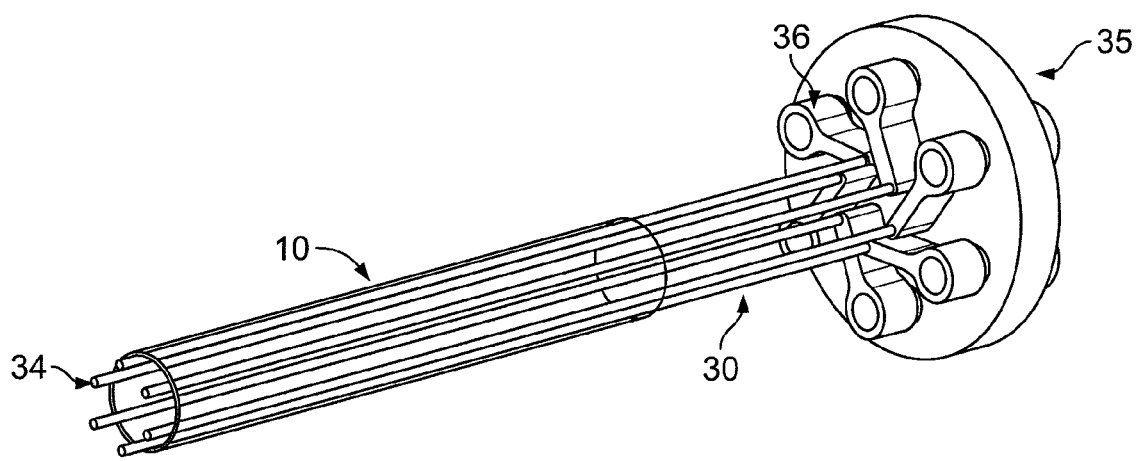
FIG. 3B is a schematic representation of the embodiment shown in FIG. 3A, the stent shown in the expanded stage.

Additionally, and as shown in FIGS. 3A-B, the expansion member can include a plurality of individual arms (34) which operatively engage followers (36) attached to a cam style end plate (35). Upon rotation of end plate (35), the followers (36) are displaced about a hinge in a clockwise direction which in turn causes the plurality of arms (34) to open or expand radially outward. Preferably, the rods (34) extend through and beyond the stent (10). Optionally, multiple stents can be loaded onto the rods of the expansion member (30) and expanded simultaneously. Further, the rods (34) can include varying geometries, for example a stepped or tapered configuration, to assist in forming the stent into a particular shape if so desired. Similarly, the rods (34) can be expanded at varying rates with respect to each other, or to differing radial distances if so desired.

In accordance with another embodiment of the invention, the expansion member can be configured as a plurality of wires which extend beyond the proximal and distal ends of the stent. Similar to the embodiments disclosed above, a mandrel can be axially inserted into an end of the plurality of wires. Preferably, the mandrel is configured with a gradual taper along the longitudinal axis which imparts an increasing radial expansion force which corresponds to the amount of axial insertion within the plurality of wires. Alternatively, a mandrel having a diameter which increases in a stepwise fashion can be employed. In one example, the mandrel is axially inserted into the distal end of the plurality of wires from the smallest diameter to largest diameter such that the taper induces a radial expansion force on the wires to force the wires to open or expand to a larger diameter. This expansion force is in turn transmitted to the stent surface, however the axial insertion force is not significantly transmitted to the stent surface. This reduction in axial force is advantageous in that it reduces the stress realized by the stent and therefore decreases the risk of strut fracture.

For purpose of illustration and not limitation, an example of the embodiment wherein the expansion member is configured as a plurality of wires is depicted in FIGS. 4A-F. FIG. 4A depicts a fixture (40) of the invention comprising an inner body (41) having a base portion (42) and an upright portion (43) configured to receive a mandrel (45). FIG. 4B depicts an outer body including a plurality of wires (44) and an anchor portion (46) for securely housing an end of the plurality of wires. In accordance with the invention, the mandrel (45) is positioned in the upright portion of the inner body (43), and a stent (10) is positioned on the outer body such that the plurality of wires (44) are inserted through the longitudinal axis of the stent. The outer body is then positioned on the free end of the mandrel (45) as shown in FIG. 4C. Next, the operator moves the outer body over the mandrel by forcing anchor portion (46) downward which in turn forces the mandrel (45) to be inserted through a receiving hole (not shown) in the anchor portion (46) and into the plurality of wires (44) and overlying stent (10) as shown in FIG. 4D.

Figure 4G:
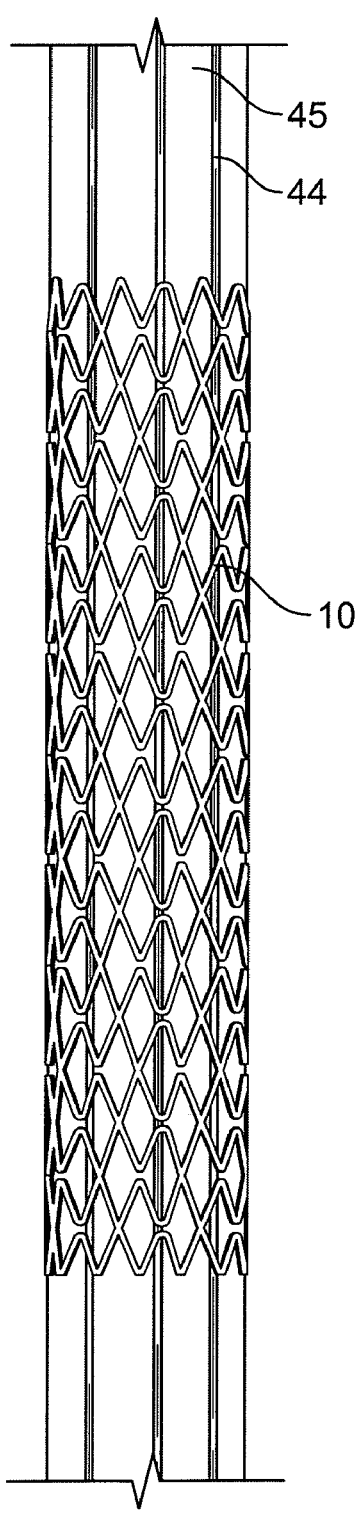

Preferably, the outer body is pulled over the mandrel until the entire stent is positioned on the mandrel with the plurality of wires (44) disposed between the stent (10) and the mandrel (45), as shown in FIG. 4G. As discussed above, the plurality of wires serve to inhibit or prevent any axial forces associated with the insertion process described above from being imparted onto the stent (10). Once the mandrel has been inserted through the entire stent, the operator secures the stent, for example by grasping with a clamp or by hand, and continues to move the outer body further down until the plurality of wires are removed from the interior of the stent. Consequently, the stent is disposed in direct contact with the mandrel for the first time during the expansion process, and can be subject to additional treatments such as polishing or heat treatment. Alternatively, the expansion process described with reference to FIGS. 4A-D can be applied to only select portions of the stent rather than the entire stent as described above, if so desired.

Figure 5A:
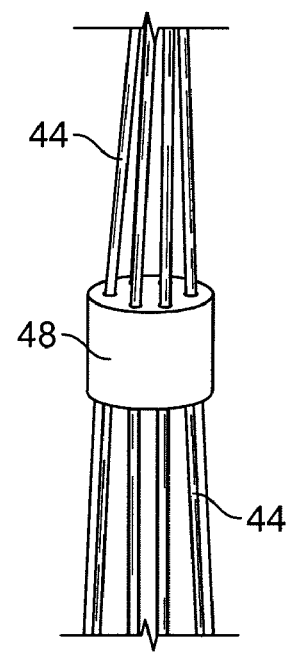
FIGS. 5A-B is a schematic representation of a mandrel in accordance with the embodiment shown in FIGS. 4A-G.
Figure 5B:
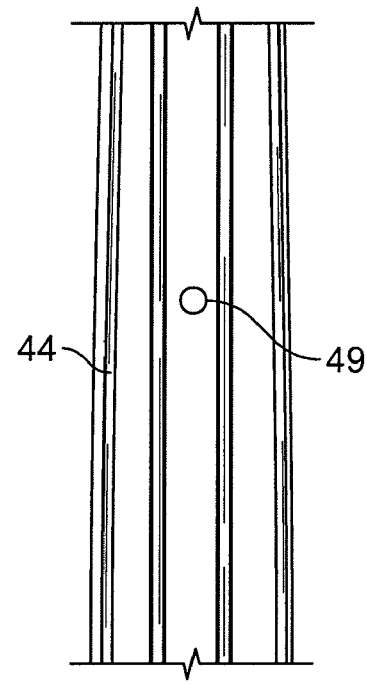

Due to the frictional forces present on the wires during the expansion process, the wires can be subject to undesirable movement or dislocation upon insertion of the mandrel. Accordingly and as depicted in FIG. 5A, a wire guide (48) can be employed having a plurality of apertures configured to receive the plurality of wires (44) of the expansion member such that the wires are maintained in a predetermined position throughout the expansion process. Thus, the presence of a wire guide ensures proper spacing of the wires throughout the expansion process to provide symmetrical displacement of the wires for forming a cylindrical stent. Additionally, the free end of the mandrel can include a notch or recess (49) for securing the wire guide thereto as shown in FIG. 5B.

A wide array of different size stents can be achieved using the apparatus and method of the embodiment disclosed in FIGS. 4A-G. For example, various stent expansion dimensions can be achieved using a plurality of mandrels having different sizes and/or taper ratios, and a fixed number of wires. Alternatively, a single mandrel can be employed to expand a plurality of stents to a wide array of different sizes wherein the number of wires is varied according to the desired expansion dimensions.

In accordance with another aspect of the invention, a plurality of rods (34), in the embodiment disclosed in FIGS. 3A-B, or wires (44) in the embodiment disclosed in FIGS. 4A-G, can be positioned adjacent to the interior surface of a stent and arranged in a generally cylindrical configuration to be supported in elongated channels (not shown) formed within a tapered mandrel (25, 45). Upon insertion of the tapered mandrel into the plurality of rods, the increasing diameter of the tapered mandrel actuates the rods to move radially outward thereby increasing the diameter of the rods. The radial movement of the rods transmits a radial expansion force on the stent to thereby increase the stent diameter. As in the various embodiments disclosed above, the axial force created by the insertion of the tapered mandrel is not significantly transmitted to the stent. Therefore, the struts and connectors (if present) are exposed to a reduced stress component which decreases the risk of fracture.

As discussed above, the stents preferred embodiment of the invention are made from Nitinol. The shape memory characteristics of such a Nitinol stent allow the stent to be deformed to facilitate their insertion into a body lumen or cavity and then be heated within the body so that the device returns to its original shape. Superelastic characteristics, on the other hand, generally allow the metal to be deformed and restrained in the deformed condition to facilitate the insertion of the medical device containing the metal into a patient's body, with such deformation causing the phase transformation. Once within the body lumen, the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

The shape memory characteristics of the invention described above are preferably imparted to the alloy under a controlled temperature environment. This temperature control serves to make the stents more ductile during the expansion process. The increase in material ductility can be achieved while exposing the stent to a temperature, for example, of approximately −40 degrees Fahrenheit. Additionally, the desired increase in material ductility can be achieved while exposing the stent to a temperature between approximately 175 and 600 degrees Fahrenheit. Consequently, the shape of the metal during this heat treatment is the shape "remembered."

The stent of the invention can be a self-expandable or balloon expandable stent having any configuration or pattern, as known to one skilled in the art. The stent body can comprise metal, metal alloy, or polymeric material. Some exemplary materials include Nitinol and stainless steel. Other complimentary materials include cobalt chromium alloy, ceramics and composites. Suitable polymeric materials include thermotropic liquid crystal polymers.

As illustrated in FIG. 1, the stent body includes a first annular element including interconnected strut members. Preferably, and as embodied herein, the stent further includes a second set of interconnected strut members defining a second annular element. The interconnected strut members can be defined by alternating stent and crown members, which define the annular element. Each annular element generally defines a structure extending circumferentially along a longitudinal axis. First and second annular elements are axially aligned along a longitudinal axis and are connected to an adjacent annular element by a plurality of connection sites.

A first annular element can include a first set of interconnected strut members that is out of phase with an axially aligned second set of interconnected strut members defining a second annular element. Alternatively, the axially aligned second set of interconnected strut members can be in phase with the first set of interconnected strut members, if desired. Further, the interconnected strut members of one annular element can be axially offset from the interconnected strut members of a second annular element.

The plurality of connection sites define a connector column and the connected annular elements define a tubular structure. Each connection site is connected at one end to one annular element and at another end to an adjacent annular element. The number of connection sites can vary, e.g., decrease or increase, from connection column to adjacent connection column along the length of the stent body, as exemplified in U.S. Pat. No. 7,112,216 to Gregorich and U.S. Pat. No. 6,113,627 to Jang, the disclosures of which are incorporated herein by reference. Thus, the number of connection sites can continuously decrease or increase along a predetermined length of the stent body. Alternatively, the number of connection sites can be constant along a predetermined length of the stent body.

The connection sites can include a variety of configurations, lengths and widths. In other words, the crowns of adjacent annular rings can be joined together to form a connection site or point. Alternatively, the connection site can have a length to define a connector strut. The connector strut can have a substantially straight or linear configuration or include at least one bend, i.e., non-linear portion.

In one embodiment of the invention, the stent body includes a first annular element comprising alternating strut and crown members axially aligned and out of phase with a the alternating strut and crown members of a second annular element. The first and second annular elements are joined at a plurality of connection sites. Additionally, the stent body can be configured with a varied flexibility along the longitudinal axis. This varied flexibility can be attained by varying the number or length of connectors, omitting struts at predetermined locations, or varying the width of the struts and/or crowns.

At least some of the connection sites extend from the center or from the side of the peak of one crown to the trough defined by the opposing crown. Alternatively, when the first set of alternating strut and crown members are in phase with the second set of alternating strut and crown members, the connection sites can extend from the peak defined by one crown to the peak defined by the opposing crown. The connection site can extend laterally or diagonally from the first set of interconnected strut and crown members.

In another aspect of the invention, the length of the connection sites can vary along the length of the stent, as could the circumferential diameter of the connection sites. For example, the stent body can include shorter and wider connection sites in an intermediate section of the stent body compared to the proximal and distal sections of the stent body. In this manner, the stent has a greater outward radial force and compression resistance in the intermediate section of the stent body, as described in U.S. Pat. No. 7,060,091 to Killion, the entire content of which is incorporated herein by reference.

The alternating strut and crown members of the annular element can define an undulating configuration or pattern along a circumferential or a longitudinal path along the stent body. Adjacent annular elements of alternating strut members and crowns can define a generally continuous wave pattern along the longitudinal axis of the stent body.

In accordance with another aspect of the invention, the stent body includes a proximal section, a distal section, and an intermediate section therebetween. Each section includes an annular element having an interconnected set of strut members. At least some of the strut members include radiopaque marker such that a radiopaque strut member is defined. The radiopaque marker can be integrated into the strut member. Alternatively, the radiopaque marker can be coated on a surface of at least some of the strut members.

Additionally, the method of reducing stress during sent fabrication and expansion disclosed herein can be employed in the manufacture of stents having various material compositions. For example, the invention can be utilized with stents formed from polymeric materials in which the expansion method discussed above minimizes the tangential surface loads imparted on the stent structure.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the invention is also directed to other embodiments having any other possible combination of the dependent features claimed below and those disclosed above. As such, the particular features presented in the dependent claims and disclosed above can be combined with each other in other manners within the scope of the invention such that the invention should be recognized as also specifically directed to other embodiments having any other possible combinations. Thus, the foregoing description of specific embodiments of the invention has been presented for purposes of illustration and description. It is not intended to be exhaustive or to limit the invention to those embodiments disclosed.

By way of example, other mechanisms for applying a mainly radial load on a stent for stent expansion can be embodied within the scope of this invention. One such embodiment may include the cylindrically arranged wires supporting the stent in a cantilever fashion, which the wires being actuated at opposite ends by two mandrels. The mandrels remain outside of the envelope of the stent structure, but provide enough radial load on the ends of the wires to urge the stent toward the expanded configuration. Obviously, this is only one permutation and many others can be envisioned that remain within the scope and intent of this invention.

Many modifications, variations, or other equivalents to the specific embodiments described above will be apparent to those familiar with the art. It is intended that the scope of this invention be defined by the claims below and those modifications, variations and equivalents apparent to practitioners familiar with this art.

What is claimed is:

1. A method of manufacturing a medical device comprising:
    forming a stent having a proximal end, a distal end, and a longitudinal axis extending therebetween, the stent having a generally cylindrical shape defining a first stent diameter;
    inserting an expansion member into the stent, the expansion member having a length extending along the longitudinal axis of the stent with at least one slot extending along at least a portion of the length of the expansion member to define a plurality of expansion blades, the expansion member having a first expansion diameter;
    inserting a mandrel into the expansion member, the mandrel extending along the longitudinal axis, the mandrel having a diameter that is greater than the first expansion diameter and greater than the first stent diameter;
    wherein the insertion of the mandrel into the expansion member radially expands the expansion member to a second expansion diameter, the radial force exerted by the radial expansion of the expansion member on the stent expands the stent to the second stent diameter, the second stent diameter being greater than the first stent diameter.

2. The method of claim 1, wherein a first portion of the expansion blades are connected at a proximal end of the expansion member and a second portion of the expansion blades are disconnected at a distal end of the expansion member.

3. The method of claim 1, further comprising axially inserting a tapered mandrel into a distal end of the expansion member to displace the blades of the expansion member and radially expand the stent to the second stent diameter.

4. The method of claim 1, further comprising exposing the stent to a temperature below approximately −40 degrees Fahrenheit to place the stent in the martensitic phase.

5. The method of claim 1, further comprising exposing the stent to a temperature within the range of approximately 175 and 600 degrees Fahrenheit.

6. A method of manufacturing a medical device comprising:
    forming a stent having a proximal end, a distal end, and a longitudinal axis extending therebetween, the stent having a generally cylindrical shape defining a first stent diameter;
    inserting a plurality of expansion members the stent, the plurality of expansion members extending along the longitudinal axis of the stent, the expansion member having a first expansion diameter;
    inserting at least one mandrel into the plurality of expansion members, the at least one mandrel extending along the longitudinal axis, the at least one mandrel having a diameter that is greater than the first expansion diameter and greater than the first stent diameter;
    wherein the insertion of the mandrel into the plurality of expansion members radially expands the plurality of expansion members to a second expansion diameter, the radial force exerted by the radial expansion of the plurality of expansion members on the stent expands the stent to the second stent diameter, the second stent diameter being greater than the first stent diameter; and
    removing the plurality of expansion members while the mandrel remains inserted within the stent.

7. The method of claim 6, wherein the plurality of expansion members are wires arranged in a generally cylindrical shape having a length which extends beyond the proximal end and distal end of the stent.

8. The method of claim 7, wherein a plurality of second stent diameters is achieved by a plurality of different size mandrels and a fixed number of wires.

9. The method of claim 7, wherein a plurality of second stent diameters is achieved by a single mandrel and a varying number of wires.

10. The method of claim 6, wherein a first cycle includes temperatures below approximately −40 degrees Fahrenheit and a second cycle includes temperatures within the range of approximately 175 and 600 degrees Fahrenheit.

* * * * *